United States Patent
Gerasimov

(10) Patent No.: US 7,139,605 B2
(45) Date of Patent: Nov. 21, 2006

(54) HEART RATE MONITOR

(75) Inventor: Vadim Gerasimov, Cambridge, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 512 days.

(21) Appl. No.: 10/391,136

(22) Filed: Mar. 18, 2003

(65) Prior Publication Data

US 2004/0186388 A1    Sep. 23, 2004

(51) Int. Cl.
*A61B 5/0245* (2006.01)
*A61B 5/0456* (2006.01)

(52) U.S. Cl. ..................... 600/519; 600/521

(58) Field of Classification Search ............... 600/509, 600/519, 521
See application file for complete search history.

(56) References Cited

U.S. PATENT DOCUMENTS

| | | | | |
|---|---|---|---|---|
| 3,939,824 A | * | 2/1976 | Arneson et al. | 600/485 |
| 4,000,461 A | * | 12/1976 | Barber et al. | 600/521 |
| 4,181,134 A | * | 1/1980 | Mason et al. | 600/502 |
| 4,790,326 A | * | 12/1988 | Mather et al. | 600/502 |
| 5,010,887 A | * | 4/1991 | Thornander | 600/509 |
| 5,243,993 A | * | 9/1993 | Alexander et al. | 600/520 |
| 5,381,803 A | * | 1/1995 | Herleikson et al. | 600/521 |
| 5,417,221 A | * | 5/1995 | Sickler | 600/509 |

* cited by examiner

*Primary Examiner*—Robert Pezzuto
*Assistant Examiner*—Yun Haeng Lee
(74) *Attorney, Agent, or Firm*—Charles G. Call

(57) ABSTRACT

A method for analyzing an EKG signal in real time to produce a heart rate indication. The most recent digitized samples of the EKG are stored in a buffer and evaluated to identify each R-wave peak sample value that (a) immediately precedes and is larger that the most recently stored digital sample value, (b) is larger than any other sample value in the buffer, and (c) differs from the first sample value in the buffer by more than a predetermined threshold value. The threshold is a fraction of the rise time slope of the last peak. The real time heart rate indication is calculated from the time duration separating the last two detected peaks, but rate indications outside the range of 30–200 beats per minute, and which depart from the preceding rate indication by more than 50 percent, are discarded.

18 Claims, 3 Drawing Sheets

HEART RATE MONITOR

BACKGROUND OF THE INVENTION

The electrocardiogram (abbreviated as either EKG or ECG) is a broadly used to obtain information ranging from a simple pulse (heart rate in beats per minute) to a very detailed description of heart activity. An EKG is obtained by recording changes in weak electrical potential coming from the heart to electrodes on the skin surface. Essentially, the EKG records an electrical side effect of heart activity. Depending on where the electrodes are placed, the changes in potential reflect depolarization and repolarization of the heart muscle along different axes. Changes in the potential along the major electrical axis of heart have a characteristic repeating pattern as shown in FIG. 1. The five visible spikes on the graph are called P, Q, R, S, and T waves. The most prominent feature of EKG graph is the tallest spike called R-wave. The top of the R-wave corresponds to the beginning of systole or ventricle contraction when blood is pumped into arteries. Heart rate is usually derived from the time difference between consecutive R-waves.

There is a need for an improved method for analyzing an electrocardiogram signal to reliably detect R-waves in order to yield a heart-rate value.

There is a particular need for an R-wave detection method that provides superior performance in applications where the electrocardiogram signal is used to monitor the heart rate of people engaged in physical activity. The R-wave detection method should accordingly be accurate in the presence of noise, including the presence of (1) motion artifacts from body muscle depolarization and repolarization; (2) changes in contact features between the electrodes and the skin; and (3) changes in overall amplitude and average level of the signal due to breathing or other phenomena that affect body conductance.

It is further desirable that the R-wave detection method exhibit a low detection latency so that it responds quickly to changing heart rates.

It is also desirable that the detection method be implemented with low cost components of small size.

SUMMARY OF THE INVENTION

In a principal aspect, the present invention takes the form of a method for detecting R-waves in an electrical signal generated by the heart. The method processes digitized samples of an electrocardiogram signal to determine the timing of the top of the R-wave that coincides with the maximum depolarization activity in the ventricles of the heart.

The detection method repetitively determines the slope of the EKG signal within a predetermined time period equal to the normal R-wave rise time (approximately 30 ms). Samples of the electrocardiogram signal are received one-by-one and stored in a multi-sample buffer (e.g., 8 samples at a sampling rate of 250 samples per second) in order to calculate the instantaneous slope of the signal. If the first derivative of the signal stays positive for an entire buffer of data and then changes to negative for another sample, a peak is detected.

If the amplitude of a detected peak is greater than the current threshold value, it is considered to be an R-wave. The threshold value against which the newly detected peak is compared is a fraction (e.g. two-thirds) of the previously detected peak amplitude. If the algorithm fails to detect any peaks for a predetermined period of time (typically 3–4 seconds), it automatically resets the detection threshold to prevent a noise spike from setting the threshold too high to detect subsequent normal R-wave peaks.

The requirement of positive derivative in consecutive sample periods effectively rejects sharp noise spikes caused by motion artifacts. The requirement that the peak amplitude be greater than the threshold value effectively rejects T-waves and slow changes in signal due to noise.

The detection further rejects detected spikes based on the basic set of assumptions for a typical heart-rate and electrocardiogram signals. These assumptions are represented as constants and specify that the detected pulse rate should not exceed 200 beats per minute nor fall below 30 beats per minute, and the pulse rate should not change by more than 50 percent between beats.

The R-wave and heart rate detection method of the present invention provides improved noise rejection, particularly motion artifacts from body muscle activity, breathing or other phenomena. Because of improved noise rejection the detection method has superior performance in applications where a heart rate is measured for people engaged in physical activity. The method further exhibits a low R-wave detection latency and performs with little computational overhead, making it well suited for real-time processing of the electrocardiogram signal using a microcontroller.

These and other features and advantages of the present invention may be more clearly understood by considering the following detailed description of a specific embodiment of the invention. In the course of this description, frequent reference will be made to the attached drawings.

DETAILED DESCRIPTION

Figure 1:
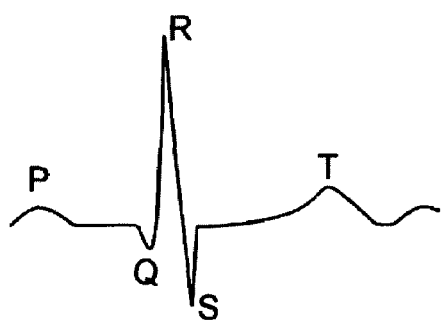
FIG. 1 illustrates a typical electrocardiogram waveform.

One of the most important measures that can be derived from the EKG is the heart rate. A noise-free EKG signal as illustrated in FIG. 1 exhibits different phases of heart activity. A heartbeat is the culmination of a contraction of the ventricles that coincides with the most prominent spike of the EKG signal, the R-wave. The heart rate is usually measured in heartbeats per minute and updated after each heartbeat as a reciprocal of the time passed after the previous heartbeat. In heart rate variability research, the time interval between R-waves is often used instead of the heart rate. The top of the R-wave spike coincides with the maximum depolarization activity in the ventricles and is the most consistent timing feature of in the EKG.

In order to convert an EKG signal to a heart-rate signal, the timing of each R-wave peak may be detected. When a person whose EKG is being measured does not move, a simple threshold value can be used to reliably recognize R-waves. Since the R-wave is normally the tallest wave, when the EKG value moves above the threshold it is reasonable to assume that this is an R-wave. The top of the wave can be detected by simply looking for the sign change in the first derivative of the signal. Because the R-wave often corresponds to the steepest slope in the signal, a detection method may alternatively compare the first derivative of the EKG signal with a threshold, and the top of the spike may be detected by finding a cross-over of the derivative from a positive to negative value.

The challenge of these approaches is how to determine the threshold values. Under ideal, noisefree conditions the threshold value can be set between the average and maximum value of the EKG signal, but noise-free conditions are hardly the norm. A fixed threshold value does not work well with real EKG signals, especially when measured on moving people. The problems include: (1) motion artifacts from body muscle depolarization and repolarization and changes in contact features between the electrodes and the skin; (2) changes in overall amplitude and average level of the signal due to breathing or other phenomena that affect body conductance; and (3) external noise, such as 50 or 60 Hz noise from the power grid. In addition, the average level, height, and shape of the R-waves drift and differ from person to person.

Some of the noise in the EKG signal can be eliminated by adjusting the parameters of the filters in the EKG amplifier circuitry, or preprocessing digitized EKG data with digital filters. For example, the noise component that is present when the EKG amplifier is not galvanically decoupled from the power grid can be eliminated with a notch filter. The other problems, including artifacts induced from muscle movement and overall changes in amplitude, are less readily addressed. Since, in many applications such as heart rate monitors used with exercise equipment, people are expected to move, an R-wave detection algorithm should be reliable in a presence of motion artifacts.

Figure 2:
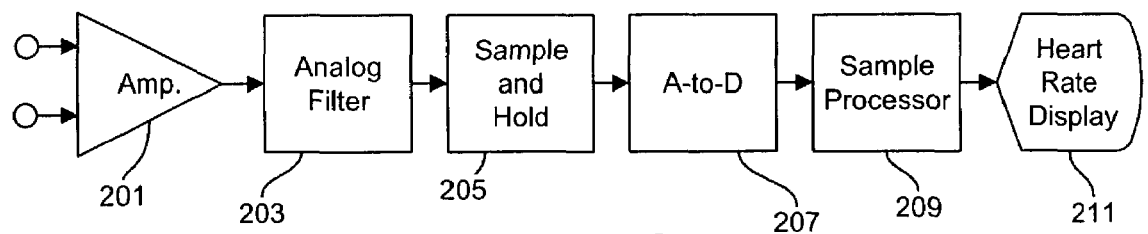
FIG. 2 is a block diagram of a conventional heart rate detector using digital EKG signal processing.

A conventional heart rate monitor is illustrated in FIG. 2. Electrodes in contact with the skin of the person being monitored provide the input signals to an analog amplifier 201. The output from amplifier 201 is passed through an analog filter 203 before being sampled by a sample-and-hold circuit 205. Analog samples from the circuit 205 are converted into digital sample values by an analog to digital converter 207. The digital samples are then processed by programmed processor at 209 to yield a heart rate (pulse) value which is displayed at 211. The sample and hold circuit 205, the A-to-D converter 207, and the programmed processor 209 may be implemented with a single integrated chip microprocessor or microcontroller.

The present invention provides an improved method for processing a digitized EKG signal in real time to produce a heart rate value. An illustrative computer program, written in Pascal, which embodies the present invention, appears at the end of this specification.

The method for detecting heart rate in the presence of noise is based on a basic set of assumptions, represented as constants program listing. These assumptions are:

(1) the maximum pulse rate is 200 beats per minute;

(2) the minimum pulse rate is 30 beats per minute;

(3) the slope to an R-wave peak must be at least 67 percent (two-thirds) of the slope to the previously detected peak; and (4) the maximum change in pulse rate between beats is 50 percent.

It is the latter two constraints on rates of change that allow the method to adapt to the relatively low-frequency variability of heart rate while filtering the relatively high-frequency artifacts due to noise.

In the illustrative embodiment set forth in the program listing below, EKG samples are delivered asynchronously 250 times per second as integer values using a dispatch mechanism which calls the ProcessEKG method of the TEKG class. The TEKG class contains an instance DetectR of the TRWaveDector class which provides three methods:

Update: which stores incoming samples in the Samples integer array, an eight cell buffer that stores eight samples stored during an interval of approximately 33 ms at the 250 sample per second sampling rate;

Spike: which returns TRUE if the necessary conditions are satisfied by the contents of the buffer to indicate receipt of an R-wave peak value; and GetSlopeToPeak: which returns the leading-edge slope to the current R-wave peak, which is saved as the variable LastR used to establish the threshold slope for the next R-wave.

Figure 3:
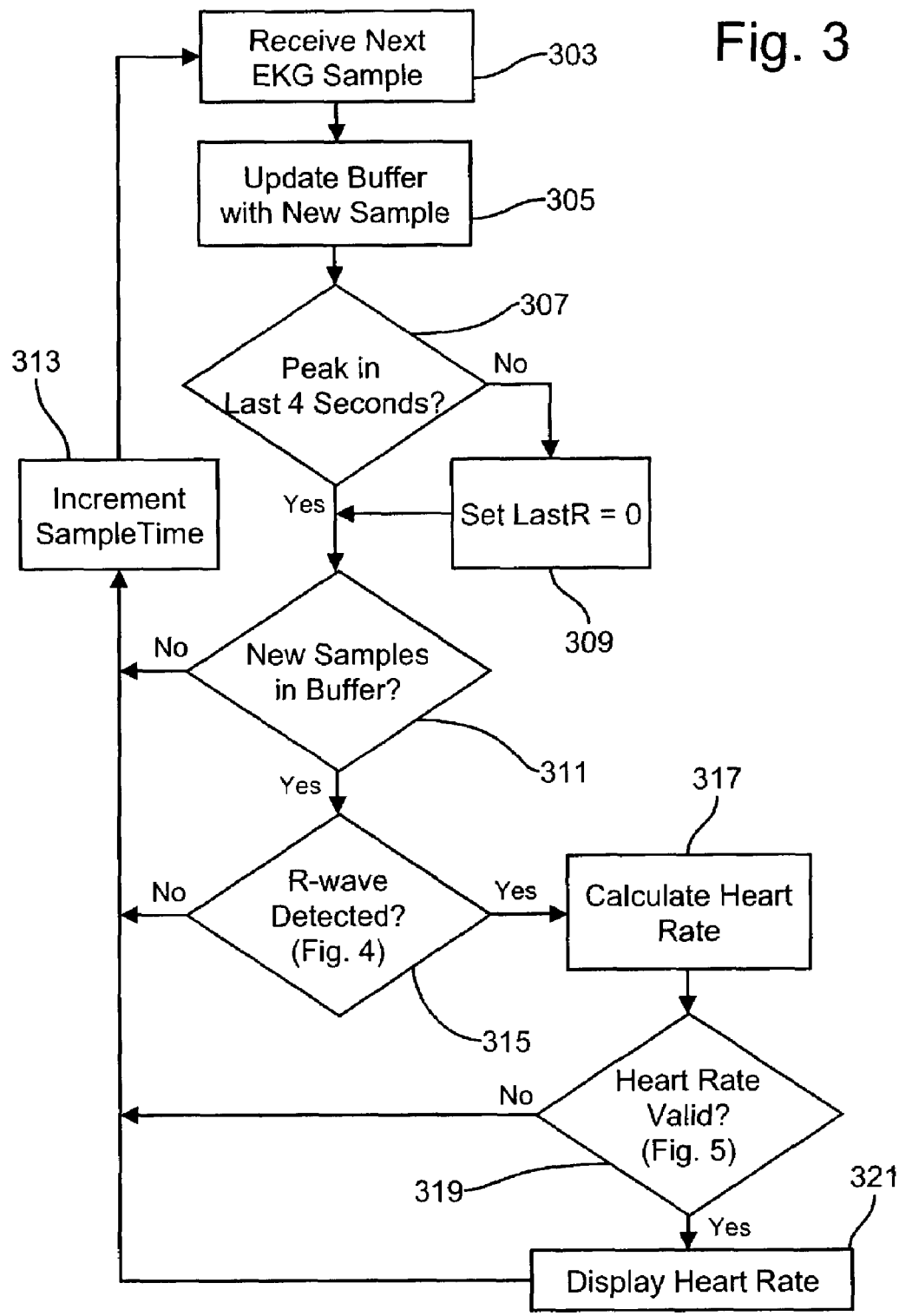
FIGS. 3–5 are flow charts illustrating an R-wave peak and heart rate detection method embodying the invention.

As depicted in the flowchart seen in FIG. 3, after placing the incoming EKG sample received at 303 in the Samples buffer by calling the Update method at 305, ProcessEKG sets LastR (the variable indicating the slope of the last detected R-wave) to zero at 309 if no R-wave peak is detected for more than 4 seconds as determined at 307 in order to recalibrate the program so that noise peaks do not continue to prevent the detection of normal R-waves.

Figure 4:
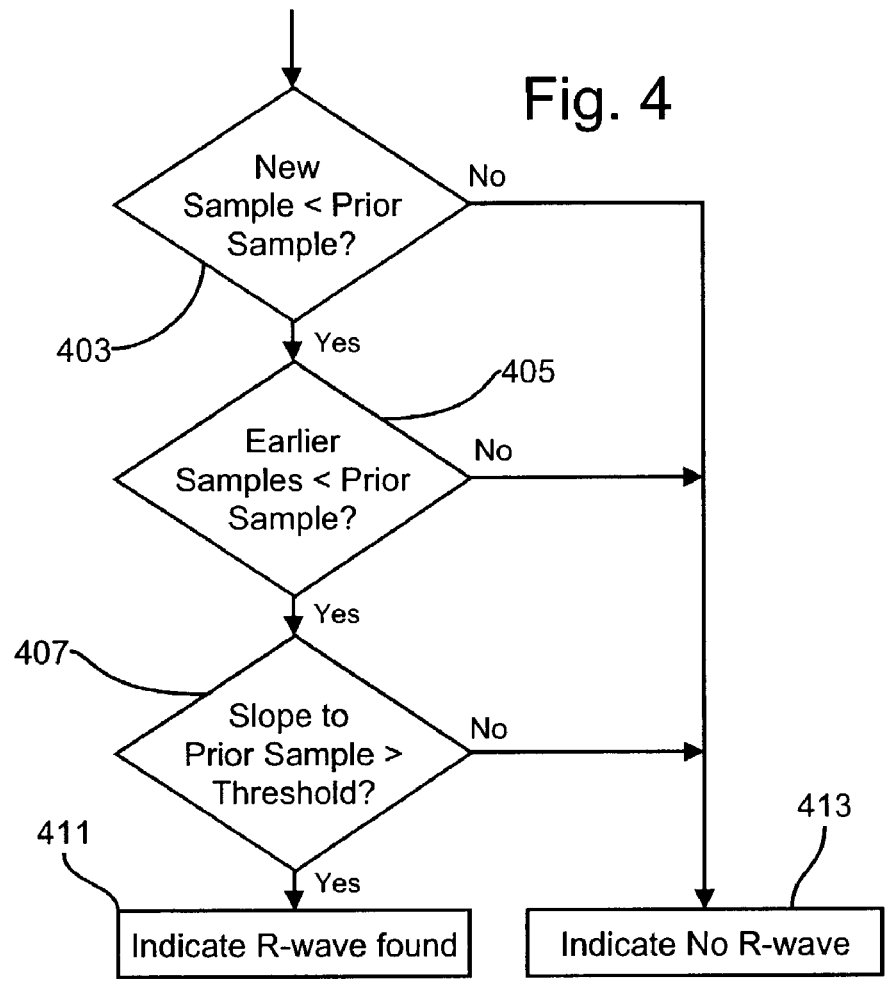

Next provided the Samples buffer contains new EKG samples received since the last R-wave was detected as determined at 311, ProcessEKG calls the Spike method at 315 to determine if the last incoming sample is the first sample after an R-wave peak. The Spike method, shown in the flowchart of FIG. 4, returns TRUE if:

the last incoming sample amplitude is less than the amplitude of its predecessor (the potential peak) as determined at 403; i.e., the waveform has past the peak and started to decrease;

all stored sample amplitudes in the sample buffer received before the potential peak are less than the amplitude of the potential peak as determined at 405; and the slope to the potential peak is greater than or equal to a threshold value equal to 67% of the slope to the previously detected peak as determined at 407. The 67% scale factor is set by the constant PeakScale.

Figure 5:
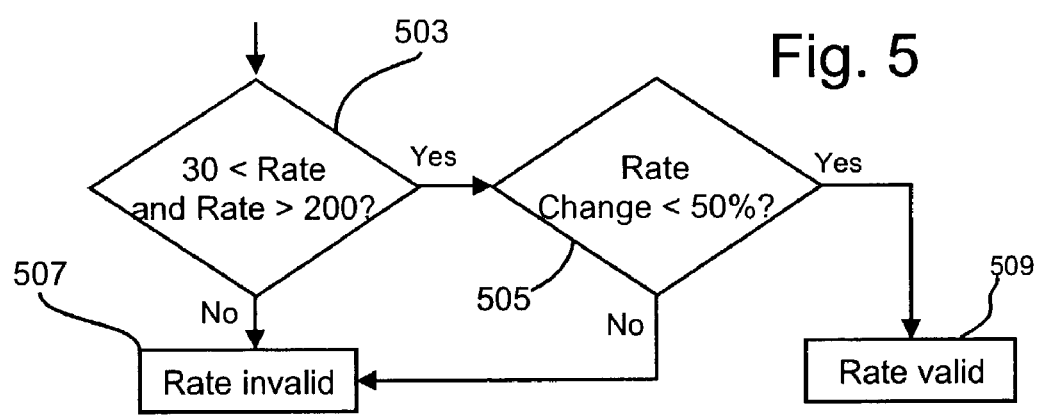

If the Spike function returns TRUE, indicating that an R-wave peak has been detected as shown at 411, the pulse rate LastPulse (a floating point value indicating beats per minute) is calculated based on the elapsed time between the last two detected R-wave peaks as seen at 317. The time and slope of the last detected peak is saved in LastRTime and LastR respectively for future use. The calculated pulse rate LastPulse is then used to update the output value Pulse (displayed at 321) provided that the tests performed as shown in FIG. 5 are satisfied; that is, provided:

the method has been running for at least three seconds;

the LastPulse value is within upper and lower limits (greater than 30 and less than 200 beats per minute) as determined at 503; and the LastPulse value did not change from the last rate (Pulse) by more than 50% as determined at 505. The 50% rate change threshold may be independently set by the constants DecreaseRatio (for rate decreases) and IncreaseRatio (for rate increases).

The variable SampleTime is incremented after each EKG sample is processed as shown at 313.

The method has been found to perform well in both real-time and post-processing applications, producing few visible motion artifacts. In a microcontroller implementation, the method requires less than 100,000 operations per second or 10% of processing power of a typical microcontroller with 4 MHz oscillator.

CONCLUSION

It is to be understood that the specific example which has been described above and set forth in detail in the following Computer Program Listing is merely illustrative of one application of the principles of the invention. Numerous modifications may be made by those skilled in the art.

Computer Program Listing

```
const
   SamplingRate = 250;
   PeakScale = 0.67; // at least 2/3 of the previous spike
   MaxPulse = 200; // maximum expected heart rate
   MinPulse = 30; // minimum expected heart rate
   DecreaseRatio = 1.5; // maximum permitted pulse rate decrease
   IncreaseRatio = 1.5; // maximum permitted pulse rate increase
   NspikeSamples:integer = SamplingRate div 30;//8 samples,~33 ms
      slope
(* TEKG class fields:
SampleTime: integer; //sample counter incremented with each valid
   sample
LastRTime: integer; //holds sample count when last R-wave detected
LastR: integer; // holds slope to last R-wave spike
Pulse: real; // output: last detected pulse rate in beats per minute
Samples: array[0..pred(NspikeSamples)] of integer; // sample buffer
DetectR: TRWaveDetector; // instance of peak detector class
*)
procedure TEKG.ProcessEKG (EKGSample: Integer);
      // called with each new sample
var
   i: Integer;
   LastPulse: Real;
begin
DetectR.Update(EKGSample); //shifts prior values in buffer to make
   room at end
if (SampleTime-LastRTime>4*SamplingRate) then LastR:=0;
   // Sets LastR to zero if no spikes detected for 4 seconds
if (SampleTime>LastRTime+NSPikeSamples) and
   // if buffer holds new samples since last R-wave and
DetectR.Spike(Round(LastR*PeakScale)) then
   // if the prior sample was a peak then
      begin
         LastPulse:=(60/(SampleTime-LastRTime))*SamplingRate;
            // calculate LastPulse = pulse rate in beats per minute
         LastRTime:=SampleTime; // replace with current R-wave time
         LastR:=DetectR. GetSlopeToPeak; // save slope to current R-wave
            peak
         if (SampleTime > 3*SamplingRate) and
            // if running for at least 3 seconds and
            (LastPulse<MaxPulse) and (LastPulse>MinPulse) and
               //  LastPulse is within limits and
            ((LastPulse<Pulse) and (Pulse<DecreaseRatio*LastPulse)) or
               // LastPulse was slower than current pulse, but not by too much or
            ((LastPulse>Pulse) and (LastPulse<IncreaseRatio*Pulse))
               // Last Pulse was faster than current pulse, but not by too much
            then Pulse:=LastPulse; // reset pulse if conditions satisfied
      end;
Inc(SampleTime); // increment sample count
end;
function TRWaveDetector. GetSlopeToPeak: Integer;
begin
Result:=Samples[NSpikeSamples-2]-Samples[0];
   // Samples[NSpikeSamples-2] holds peak;
   Samples[NSpikeSamples-1] = 1st dip
end;
function TRWaveDetector.Spike (Threshold: Integer): Boolean;
var
   i: Integer;
begin
Result:=False;
if Samples[NSpikeSamples-2]=Samples[0] then Exit; // no increase
   over base
for i:=0 to NSpikeSamples-3 do
   if Samples[i]>Samples[NSpikeSamples-2] then Exit;
      // returns false if any prior sample before possible peak > than possible
         peak
if (Samples[NSpikeSamples-1]>=Samples[NSpikeSamples-2]) then exit;
   //returns false if current sample not less the predecessor (possible peak)
if (Samples[NSpikeSamples-2]-Samples[0]) < Threshold) then Exit;
   // returns false if slope of possible peak is less than
   // threshold (67% of slope to last detected peak)
Result:=True;
end;
procedure TRWaveDetector.Update(Sample: Integer);
var
   i: Integer;
begin
for i:=0 to NSpikeSamples-2 do Samples[i]:=Samples[i+1];
   // shift buffer contents one position to make room at end of buffer
Samples[NSpikeSamples-1]:=Sample;
   // put incoming sample at end of buffer
end;
```

What is claimed is:

1. The method of determining a heart rate from an electrocardiogram signal comprising the steps of:
   detecting the occurrence of a series of R-wave peaks in said signal at the times:
   a) when said signal begins to decrease after having increased during an immediately preceding time interval at a rate of change greater than a threshold rate of change to reach a peak value, and
   b) when said peak value has a greater amplitude than the amplitude of said signal at any other time in said immediately preceding time interval,
   calculating a series of heart rate values from the durations separating adjacent ones of said detected R-wave peaks, and
   discarding any heart rate value which differs from the preceding heart rate value by more than a predetermined amount.

2. The method as set forth in claim 1 wherein said threshold rate of change is a predetermined fraction of the rate of change of said signal during a time interval immediately preceding the time at which the prior R-wave peak was detected.

3. The method as set forth in claim 2 for further discarding any heart rate value that is less than a predetermined minimum.

4. The method as set forth in claim 3 for further discarding any heart rate value that is greater than a predetermined maximum.

5. The method as set forth in claim 1 for further discarding any heart rate value that is less than a predetermined minimum.

6. The method as set forth in claim 5 for further discarding any heart rate value that is greater than a predetermined maximum.

7. A method for deriving a heart rate value from an electrocardiogram signal having a waveform exhibiting a series of R-wave peak values, said method comprising, in combination the steps of:
   producing an indication that an R-wave peak has occurred:
      when the amplitude of said waveform decreases immediately after reaching a given one of said peak values;
      when the amplitude of said given one of said peak values is larger than the amplitude of said waveform at any time in a predetermined interval immediately preceding the occurrence of said given one of said peak values, and when the rate of change of the amplitude of said waveform during said predetermined time interval is greater than a threshold value, and calculating heart rate values from the measured time interval between said peak time positions.

8. The method as set forth in claim 7 wherein said threshold value is a predetermined fraction of the rate of change of said signal during a time interval immediately preceding the previously determined peak time.

9. The method as set forth in claim 8 for further discarding any heart rate value that is less than a predetermined minimum.

10. The method as set forth in claim 9 for further discarding any heart rate value that is greater than a predetermined maximum.

11. The method as set forth in claim 7 for further discarding any heart rate value that is less than a predetermined minimum.

12. The method as set forth in claim 11 for further discarding any heart rate value that is greater than a predetermined maximum.

13. The method for analyzing a continuous electrocardiogram signal to produce a numerical pulse rate indication in real time, said method comprising, in combination, the steps of:

producing digital sample values representing samples of said signal taken at a predetermined sampling rate, storing a series of the most recently produced ones of said digital sample values, evaluating said series to identify a peak sample value that (a) immediately precedes and is larger than the most recently stored digital sample value, (b) is larger than any other sample value in said series, and (c) differs from the first sample value in said series by more than a predetermined threshold amount, and determining said numerical pulse rate indication from the time duration separating consecutive ones of said peak sample values.

14. The method as set forth in claim 13 further includes the step of establishing a new threshold amount equal to a predetermined fraction of the amount by which an identified peak sample value differs from the first sample value in said series.

15. The method as set forth in claim 14 for further discarding any heart rate value that is less than a predetermined minimum.

16. The method as set forth in claim 15 for further discarding any heart rate value that is greater than a predetermined maximum.

17. The method as set forth in claim 13 for further discarding any numerical pulse rate indication that is less than a predetermined minimum.

18. The method as set forth in claim 17 for further discarding any numerical pulse rate indication that is greater than a predetermined maximum.

* * * * *